Sept. 22, 1959 F. B. ROCHE Plant Pat. 1,867
PLUM TREE
Filed April 12, 1957
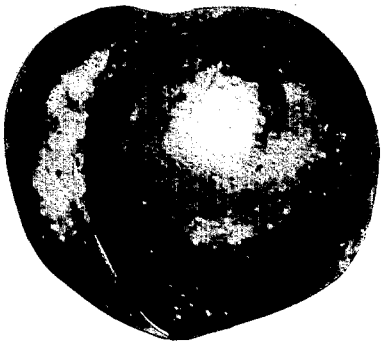
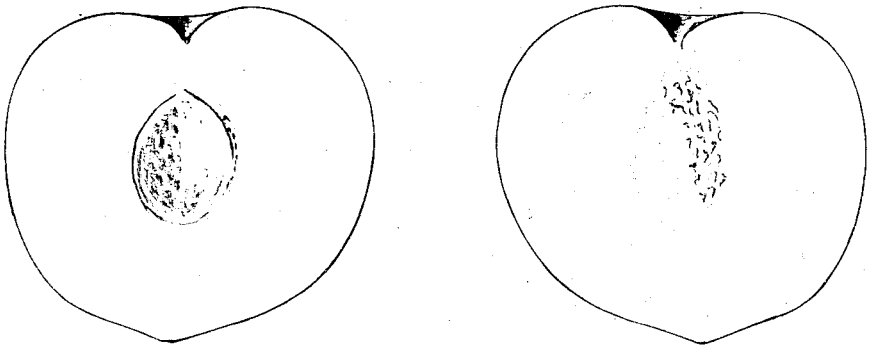

United States Patent Office

Plant Pat. 1,867
Patented Sept. 22, 1959

1,867

PLUM TREE

Franklin Bolton Roche, Oakland, Calif.

Application April 12, 1957, Serial No. 652,637

1 Claim. (Cl. 47—62)

The present discovery relates to a new and distinct variety of plum tree, originating as a chance seedling found growing in my home orchard in Oakland, California.

This variety having much the same growing habits as the parent variety, distinctively differs therefrom in coloring of the skin and flesh of the fruit. Whereas the stone is of similar size and shape as the parent tree it is absolutely a freestone. This new variety also ripens from six to ten days earlier than the parent tree.

Asexual reproduction by means of top working onto seedlings conducted by myself in my home orchard in Oakland, Alameda County, California, shows that the characteristics hold true through succeeding propagations.

In the drawings is shown a perspective view of one of the fruit of the new variety, together with one fruit split in half showing stone exposed in one half and the pit in the other half. Referring now more specifically to the pomological details of this new and distinct variety of plum tree, the following is an outline description thereof; all major color plate identifications being by reference to Maerz and Paul Dictionary of Colors.

Tree: Medium size; vigorous; semi-spreading; rapid grower; hardy; very productive; regular bearer.

Trunk: Medium; medium rough caused by elongated growth slits in the bark.

Branches: Medium; smoother than the trunk; medium branching.

Leaves: Average length 4½ inches; average width 2⅛ inches; medium size; medium length; medium width; elliptic-ovate and short-acuminate shape; medium thick, dull green; medium smooth. Margin—obtusely serrate. Petiole—medium length; medium thick.

Flowers: Blooms at the same time as its parent tree, the Satsuma, of which it is a sport.

Fruit: Matures 6 to 10 days later than the Santa Rosa, and 6 to 10 days earlier than the Satsuma. The fruit is almost completely colored up when hard ripe, and it is eating ripe about four days after it is in common storage. It has never been placed in cold storage. Size—axial diameter averages 2⅛ inches; transverse averages 2¼ inches. Form—round, slightly flattened and indented at the stem end. Suture—slight depression beyond pistil point. Cavity—tinged with red-yellow. Stem—medium; adheres firmly. Skin—medium thick; smooth; almost non-acid. Color—purplish-blue over all color. More specifically describing the color of this fruit according to the Maerz and Paul Dictionary of Colors, plate 46 K–11 when hard ripe, and plate 46 J–12 when eating ripe. Dots—rather inconspicuous; small; round and paler than the skin coloring; distribution of dots; medium in number.

Flesh: Tinged with red-yellow near pit cavity; light yellow, fading out towards the skin. According to Maerz and Paul Dictionary of Colors, plate 9 K–4 to J–1.

Juice: Abundant and sweet.

Texture: Medium firm with irregular fiber-like veins of approximately ¼ inch in length.

Ripens: Evenly.

Flavor: Deliciously delicate.

Eating quality: Very good to best.

Use: Fresh fruit; dessert; culinary.

Stone: Freestone; small oblate, approximately ⅝ inch across and ⅜ inch thick. No tendency to split.

Keeping quality: Medium.

Resistance to insects: No pests have attacked it to date, controlled by conventional commercial spray practices.

Disease: Appears to be resistant; using conventional commercial spray practices no disease has developed to date even though peaches and Santa Rosa plums in the same orchard have to be sprayed for brown rot.

The tree and its fruit herein described may vary in slight detail due to climatic and soil conditions under which the variety may be grown.

Having thus described my invention, I claim:

A new and distinct variety of plum tree substantially as described and illustrated, bearing large, firm, yellow fleshed freestone fruit with purplish blue skin, with rather inconspicuous round dots which are paler than the skin coloring; such fruit ripening approximately 6 to 10 days later than the Santa Rosa plum and 6 to 10 days earlier than the Satsuma plum, and being round, slightly flattened and indented at the stem end.

References Cited in the file of this patent

Publication: Released Notice (1954): To Fruit Growers and Nurserymen Relative to the Introduction of Four New Plum Varieties. (Laroda, etc.) P. F. Sharp and F. P. Cullinan. Agricultural Experiment Station, U. of California, Davis, California, and U.S. Department of Agriculture, Agricultural Research Service Horticultural Crops Research Branch.